(12) United States Patent
Odom et al.

(10) Patent No.: US 6,451,616 B1
(45) Date of Patent: Sep. 17, 2002

(54) ANALYSIS OF MOLECULES BOUND TO SOLID SURFACES USING SELECTIVE BOND CLEAVAGE PROCESSES

(76) Inventors: Robert W. Odom, 2068 Harvard St., Palo Alto, CA (US) 94306; Kuang Jen Wu, 1488 Rose Garden La., Cupertino, CA (US) 95014

( * ) Notice: Subject to any disclaimer, the term of this patent is extended or adjusted under 35 U.S.C. 154(b) by 0 days.

(21) Appl. No.: 09/424,177

(22) PCT Filed: May 15, 1998

(86) PCT No.: PCT/US98/10120

§ 371 (c)(1),
(2), (4) Date: Nov. 19, 1999

(87) PCT Pub. No.: WO98/53296

PCT Pub. Date: Nov. 26, 1998

Related U.S. Application Data (60) Provisional application No. 60/047,040, filed on May 19, 1997.

(51) Int. Cl.[7] ............................................... B01D 59/44
(52) U.S. Cl. ...................... 436/173; 250/288; 250/425; 250/423 P; 436/177; 436/178; 436/181
(58) Field of Search .................. 436/173, 177, 436/178, 181; 250/282, 288, 425, 423 P (56) References Cited

U.S. PATENT DOCUMENTS

| | | |
|---|---|---|
| 5,118,937 A | 6/1992 | Hillenkamp et al. |
| 5,294,465 A | 3/1994 | Gallagher |
| 5,405,743 A * | 4/1995 | Tarnowski et al. |
| 5,547,835 A | 8/1996 | Koster |
| 5,719,060 A | 2/1998 | Hutchens et al. |

* cited by examiner

*Primary Examiner*—Jan Ludlow (57) ABSTRACT

A method for the chemical analysis of molecules bound and bonded to solid surfaces is presented. The method includes the steps desorbing absorbate molecules or structurally significant fragments of these molecules by selective cleavage of a bond in an absorbate/substrate system using resonant excitation processes and detection of the absorbate species or its characteristic fragments using mass spectrometry techniques.

5 Claims, 3 Drawing Sheets

ANALYSIS OF MOLECULES BOUND TO SOLID SURFACES USING SELECTIVE BOND CLEAVAGE PROCESSES

RELATED APPLICATION

This application claims the benefit under 35 U.S.C. 119(e) of U.S. provisional patent application No. 60/047,040, filed May 19, 1997 and is hereby incorporated by reference.

FIELD OF THE INVENTION

This invention relates generally to methods for the desorption and analysis of surface adsorped species. More specifically, this invention relates to desorption by selective bond cleavage using resonant energy sources such as electromagnetic radiation and particle beams.

BACKGROUND OF THE INVENTION

The advent of new technologies based on chemical reactions on solid supports has generated an ever increasing need for accurate, efficient and selective chemical analysis of atoms and molecules adsorbed onto the solid. Research and development in this area is primarily concentrated in combinatorial chemistry and ordered monolayer films (e.g. Langmuir-Blodgett and self-assembled monolayers). Depending on the technological application, these adsorbed species can be inorganic or organic compounds as well as a large array of biomolecules including proteins, peptides, oligonucleotides, DNA fragments and pharmaceutical compounds. Selective chemical analysis of surface adsorbed species often presents special difficulties since these molecules are bound to the surface and, hence, any process which attempts to remove or desorb the surface molecules has a high probability of dissociating or fragmenting the sought after species. It is often difficult to identify the original molecular species with data produced from fragmented and degraded molecules.

One method that has been used for analyzing surface adsorbed biomolecules is laser induced desorbtion followed by mass spectrometric analysis of the desorbed species. Variations on this method are described in U.S. Pat. Nos. 5,719,060, 5,118,937, 4,920,264, 5,062,935 and 4,988,879, all of which are incorporated herein by reference. While the methods disclosed in these patents have proved useful in analysis of surface adsorbed biomolecules, none of the methods include the selective cleavage of molecules from a solid surface using resonant excitation processes. As described below, such a selective, resonant method has important advantages over the methods described in these patents.

U.S. Pat. No. 5,719,060 to Hutchens, which is hereby incorporated by reference, discloses the adsorption of analyte molecules onto a probe surface followed by their subsequent laser induced desorption using ultra-violet (UV) radiation and detection using mass spectrometry. Hutchens does not disclose selective cleavage of specific adsorbate/substrate bonds using resonant energy excitation. One important drawback of using non-resonant, UV radiation is that the analyte molecules can directly absorb this radiation which could lead to fragmentation of the desorbed species. It is often critically important to avoid fragmentation of the desorbed species since this makes subsequent analysis much more difficult. A second limitation of the techniques of Hutchens and others involved in matrix assisted laser desorption/ionization (described below) is that the analyte species may resist ionization because of its inherent properties such as its ionization potential, proton affinity, hydride affinity or electron affinity.

U.S. Pat. Nos. 5,118,937, 5,062,935 and 4,920,264, each of which are hereby incorporated by reference, disclose methods in which the analyte molecules are incorporated into a matrix that absorbs laser light. In these methods, the matrix absorbs the laser light which heats the matrix and leads to thermal desorption and ionization of the analyte molecules. This ionization occurs primarily by charge transfer (electron or positive or negative ion), cationization or electron ejection processes. These ions of the analyte molecules may then be analyzed using standard mass spectrometric methods. The main drawback of these matrix-assisted methods is that the analyte molecules must form a mixture with the matrix such that the analyte can desorb with the matrix. In addition, these methods are not useful for a monolayer or few monolayers of analyte bound to a solid support.

U.S. Pat. No. 4,988,879 to Zare, et al. discloses an apparatus and method for laser desorption and volatilization of molecules and is here by incorporated by reference. In this method, analyte molecules are physisorbed onto a solid support that can absorb laser light. When irradiated with the desorbing laser, the support absorbs the laser light which heats the support and leads to thermal desorption of the analyte molecules. This method is a thermal desorption process which does not attempt to selectively desorb the analyte molecules. In addition, this method could lead to extensive fragmentation of thermally sensitive biomolecules which could significantly impede their identification with the method.

In sum, the previously disclosed methods require either a matrix or support that can absorb laser light to induce thermal desorbtion and are all limited to non-selective or non-resonant laser excitation. The present invention is a new method for analysis of surface adsorbed molecules that overcomes the drawbacks of these previous methods. Specifically, the present invention allows the desorption of intact molecules as opposed to fragments. The method should achieve a very high yield of desorbed, intact molecules—one or more orders of magnitude higher than any other known technique. Using the present method the chemical noise in the analysis of the desorbed, intact molecules may be orders of magnitude lower than with existing techniques, permitting, in principle, orders of magnitude higher detection limits for molecules bound to surfaces.

SUMMARY OF THE INVENTION

The present invention provides a method for the selective, specific chemical analysis of molecules bound or bonded to solid surfaces. The general method includes the steps of (1) selecting an electromagnetic wavelength that is approximately resonant with an energy transition between two or more energy states of the chemical bonds at the surface of an absorbate/substrate system and (2) irradiating the surface of this absorbate/substrate system with the electromagnetic radiation to effect selective dissocation or bond breakage of specific chemical bonds at or near the surface of the absorbate/substrate system. The method can include the additional step of detecting the absorbate by mass spectrometry.

The selective cleavage of a bond in the adsorbate/substrate system may be accomplished by irradiating the system with electromagnetic radiation or by bombarding the system with a particle beam. In one embodiment, the system may be both irradiated with electromagnetic radiation and bombarded with a particle beam.

In the embodiment using electromagnetic radiation, the wavelength of the radiation is selected to be approximately resonant with a transition between two energy levels in the adsorbate/substrate system. These energy levels may be separated by an electronic, vibrational, or rotational transition or some combination of these transitions. Irradiation of the adsorbate/substrate system with electromagnetic radiation at the selected wavelength will lead to cleavage of a bond in the adsorbate/substrate system and desorption of the adsorbate. It is preferred to use a laser to irradiate the adsorbate/substrate system and it is more preferred to use a pulsed laser. It is most preferred to use a laser in the infra-red region of the spectrum.

The bond cleaved in adsorbate/substrate system by the resonant excitation can be due to physisorption, ionic or covalent(chemisorption) interactions between the analyte molecule and elements or molecules in the substrate. Bond cleavage can be one or more of the bonds of the absorbate to the substate or a bond removed from the adsorbate/substrate bond. Alternatively, the cleaved bond can be a bond within the substrate that is at a position removed from the adsorbate/substrate bond.

Generally, any substrate capable of forming physisorbed, ionic or covalent bonds with the adsorbate may be used.

Preferred substrates include glass, metal, semiconductor, and carbonaceous substrates. A preferred substrate is glass, in which case the adsorbate may be bonded to the substrate via one or more silicon atoms and/or one or more oxygen atoms. In a preferred embodiment, the adsorbate contains a silicon atom bonded to one or more silicon oxide moieties on the substrate surface. This may be represented as S—Si—O—Si—R where S represents the remainder of the substrate and R represents the remainder of the adsorbate. In this embodiment, a preferred resonant transition to be excited is the asymmetric stretch of the Si—O—Si— group. Excitation of this transition may lead to cleavage of either the substrate/adsorbate, —O—Si—R bond or bonds within the substrate. In this embodiment of the invention, it is preferred that wavelength selected is between about 8.85 micrometers and about 10.00 micrometers. It is also preferred that the laser is a pulsed laser with a pulse width of less than about one millisecond.

In an alternative embodiment the resonant excitation may be accomplished by bombarding the adsorbate/substrate system with a particle beam having an energy approximately equal to the transition between the energy levels in the adsorbate/substrate system. Suitable particles include electrons, positrons, positive elemental ions, negative elemental ions, neutral atoms, positive molecular ions, negative molecular ions, positive cluster ions, negative cluster ions, and neutral molecules.

DETAILED DESCRIPTION OF THE INVENTION

To ensure a complete understanding of the invention the following definitions are provided:

Adsorbate: Absorbate is a bound or bonded molecular species.

Susbstrate: Substrate is a solid surface to which an adsorbate is bound or bonded.

Physisorption/Physisorbed: Physisorption/Physisorbed is an abbreviation for physical adsorption and refers to weak, van der Waals interactions (dispersion, or a dipolar interactions) between a substrate and adsorbate in which the energy of interaction is on the order of the enthalpy of condensation of the adsorbate onto the substrate which is approximately 20 kJ/mol (kilojoules per mole).

Chemisorption/Chemisorbed: Chemisorption/Chemisorbed is an abbreviation for chemical adsorption; and refers to adsorbates bound to substrate through true chemical bonds either ionic or covalent. Interaction energy for these bonds is on the order of conimon chemical bonds and the enthalpy of a chemisorbed bond is on the order of 200 kJ/mol.

Laser: Laser refers to light amplification by stimulated emission of radiation and refers to devices which provide provide high intensity, nearly monochromatic light at various light wavelengths or frequencies.

Pulsed Laser: Pulsed laser refers to a laser whose output comes in packets or pulses in time. The irradiance (number of photons emitted per unit area-unit time) of pulsed lasers is generally much higher than the irradiance of continuous or non-pulsed lasers.

Electromagnetic Radiation: Electromagnetic radiation refers to the energy emanating from oscillation of transverse electric and magnetic fields. Electromagnetic radiation is characterized by a wave of disturbance of wavelength, $\lambda$, which is the distance between peaks of the wave and its frequency, $\nu$, the number of times the wave returns to its original displacement per unit time as it passes a fixed point.

Particle Collision: Particle collision refers to the physical collision of an atomic or molecular species with itself. Particles also refer to sub-atomic entities such as electrons and positrons. Particle collision also refers to physical scattering or chemical reactions occurring during or after the interaction of the electromagnetic or nuclear fields of two or more particles.

Particle Bombarding: Particle bombarding refers to physical or chemical processes by which particles are put into collisions.

Impact Electron Ionization: Impact electron ionization refers to ionization of neutral atoms or molecules achieved by passing an energy beam of electrons through a gas environment which contains the atoms or molecules. Electron impact ionization generally forms singly or multiply charged positive ions (i.e., those which have lost one or more electrons) from the neutral atoms or molecules. The mechanism of this ionization is the quantum mechanical interaction of a fast electron with one or more of the valence electrons in the atom or molecule to be ionized.

Resonance Ionization: Resonance ionization refers to the ionization of atoms and molecules by supplying same with external electromagnetic radiation tuned to a frequency similar to or identical with the frequency(ies) of one or more quantum mechanical energy levels in the atom or molecule. The irradiance of this external source of electromagnetic energy must be sufficient to cause ionization, either directly through absorption of sufficient irradiance of electromagnetic radiation or indirectly by chemical reaction of the atoms or molecules. The external source of electromagnetic radiation covers the known electromagnetic spectrum and also includes charge and neutral particle bombardment of atoms or molecules.

Chemical Ionization: Chemical ionization refers to the ionization of neutral atoms or molecules by collision of same with another particle which readily releases or accepts charged particles including electrons, protons and gas phase acids and bases.

Charge Transfer Ionization: Charge transfer ionization refers to the transfer of charge from one atomic or molecular species to another during particle collisions.

Positron: Positron is the sub-atomic particle which is the anti-particle of the electron thus it has the same mass as the electron but different charge.

Taking into account these definitions, the present invention is directed to methods and processes for the chemical analysis of molecules bound to solid surfaces.

In accordance with this invention, adsorbate/substrate bonds are divided into two general classes: physisorbed and chemisorbed. The bonding of an adsorbate to a surface can involve multiple bonds between the two moieties. This invention discloses a method to selectively break or cleave physisorbed and/or chemisorbed bonds using resonant excitation processes in which energy (excitation) is directly coupled into specific or resonant energy states of adsorbate/substrate bond(s) resulting in dissociation and liberation of an adsorbate from the surface. This invention also relates to resonant excitation and cleavage of selected bonds within the adsorbate moiety at positions removed from the substrate/adsorbate bond. These bonds will be referred to as adsorbate bonds. This invention further relates to resonant excitation of selected bonds within the substrate at positions removed from the substrate/adsorbate bond. These bonds will be referred to as substrate bonds.

Adsorbate/substrate Systems

Resonant excitation processes refer to coupling an external source of energy into adsorbate/substrate bonds at allowed electronic, vibrational or rotational transitions of one or more of these bonds. Selective bond cleavage processes can be applied to substrate-adsorbate bonds formed from a large number of elemental species. Examples of these bonds include, but are not limited to the following:

Glass Substrate/Adsorbate

Bonds between a glass substrate and adsorbate species may be cleaved by the processes of this invention. Examples of these bonds include but are not limited to:

In these formulae, the "s" subscript refers to the substrate atom(s); the "a" subscript refers to the adsorbate and the symbol "⇋" refers to the position of the bond cleavage. "R" refers to an inorganic or organic moiety attached to the adsorbate atom which is bound to the surface.

Metal Substrate/Adsorbate

Bonds between a metal substrate and adsorbate species may be cleaved by the processes of this invention. Examples of these bonds include but are not limited to:

In these formulae, "M" denotes the elemental metal in the substrate; "s" subscript refers to the substrate atom(s); the "a" subscript refers to the adsorbate and the symbol "⇋" refers to the position of the bond cleavage. "R" refers to an inorganic or organic moiety attached to the adsorbate atom which is bound to the surface.

Carbonaceous Substrate/Adsorbate

Bonds between a carbonaceous substrate and adsorbate species may be cleaved by the processes of this invention. Examples of these bonds include but are not limited to In the formulae "C" denotes elemental carbon in the substrate; the symbol "≈" denotes single or multiple bonds of the carbon substrate atom with its adjacent species; "X" refers to some element other than oxygen (0) or carbon (C) bound to the substrate carbon; "s" subscript refers to the substrate atom(s); and the "a" subscript refers to the adsorbate. Bond cleavage can occur at the =bond position or at the symbol ⇋. "R" refers to an inorganic or organic moiety attached to the adsorbate atom which is bound to the surface. Inorganic adsorbates could include metals and metal oxides such as Au, FeO, $CrO_2$, etc., inorganic salts such as NaCl and $AgNO_3$, etc. as well as many inorganic/organic complexes. Organic adsorbates include carboxylic acids, ethers, alcohols, amines, amides, esters, sugars, amino acids, peptides, proteins and oligonucleotides among others.

Methods for Selective Bond Cleavage

Processes which can couple energy into the cleavage of adsorbate/substrate bonds discussed above include the following:

1. Vibrational or vibrational/rotational excitation of adsorbate/substrate bond(s).

2. Electronic excitation of adsorbate/substrate bonds. This electronic excitation may cleave the adsorbate/substrate bond or it may be necessary to follow electronic excitation with an auxiliary technique such as selective vibrational or vibrational/rotational excitation of the electronically excited adsorbate/substrate bond(s) during the lifetime of this electronic excitation.

3. Vibrational or vibrational/rotational excitation followed by electronic excitation in which the electronic excitation is coupled into the vibrational/rotational excited state during its characteristic lifetime.

Figure 1:
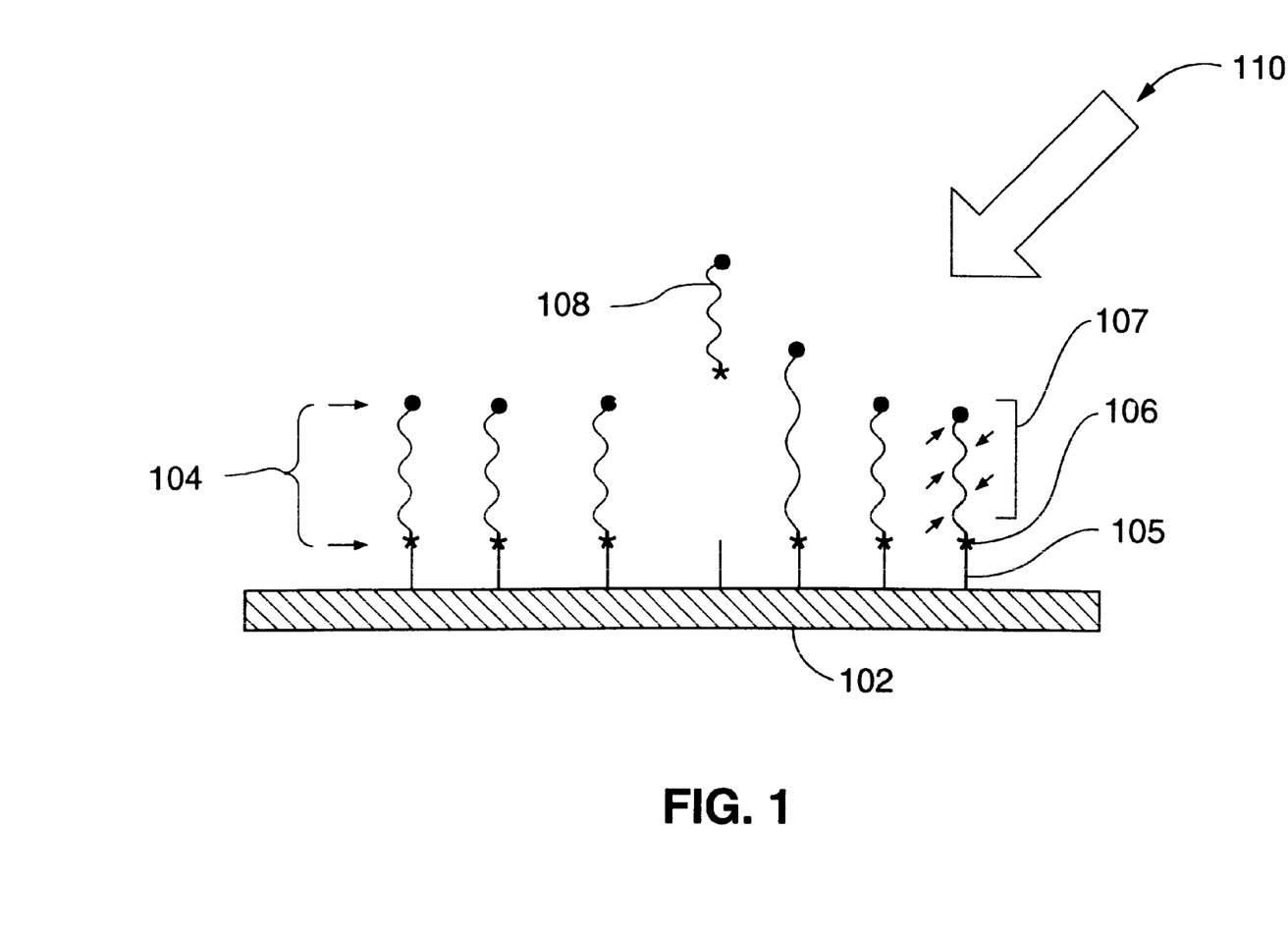
FIG. 1 shows a schematic cross-section of one embodiment of the present invention.

Methods to achieve selective excitation of the adsorbate/substrate bond(s) which cleave adsorbates from the substrate include excitation by absorption of electromagnetic radiation or excitation by collision of energetic particles onto the adsorbate/substrate surface. FIG. 1 is a schematic diagram of these basic processes in which cleavage of adsorbate/substrate bonds are produced by absorption of electromagnetic radiation or by projectile or particle collision processes.

FIG. 1 includes a substrate 102, absorbate bonds 107 and substrate bonds 105. Bound absorbate is bound to the substrate 102 by a substrate/absorbate bond 106. The substrate/absorbate bond 106 is cleaved by irradiation for selective disassociatation 110 thereby releasing cleaved absorbate 108. Alternatively, a substrate-substate or adsorbate-adsorbate bond may be selectively broken giving rise to distinctive molecules or fragments of molecules diagnostic of the presence of adsorbate species bound to the surface.

Selective Bond Cleavage Using Resonant Electromagnetic Radiation

Preferred embodiments of resonant excitation leading to selective cleavage of adsorbate/substrate bonds include:

In one embodiment, absorption of multiple infrared photons of electromagnetic radiation into specific vibrational/rotational states using infrared lasers tuned to one or more vibrational/rotational transitions of selected adsorbate/substrate bonds can be utilized. As is well known in the art, absorption of photons will occur even when the frequency of the electromagnetic radiation is not exactly resonant with a vibrational/rotational transition. One of ordinary skill in the art will know how much the laser frequency can be off-resonance without substantially diminishing the absorption.

Figure 2:
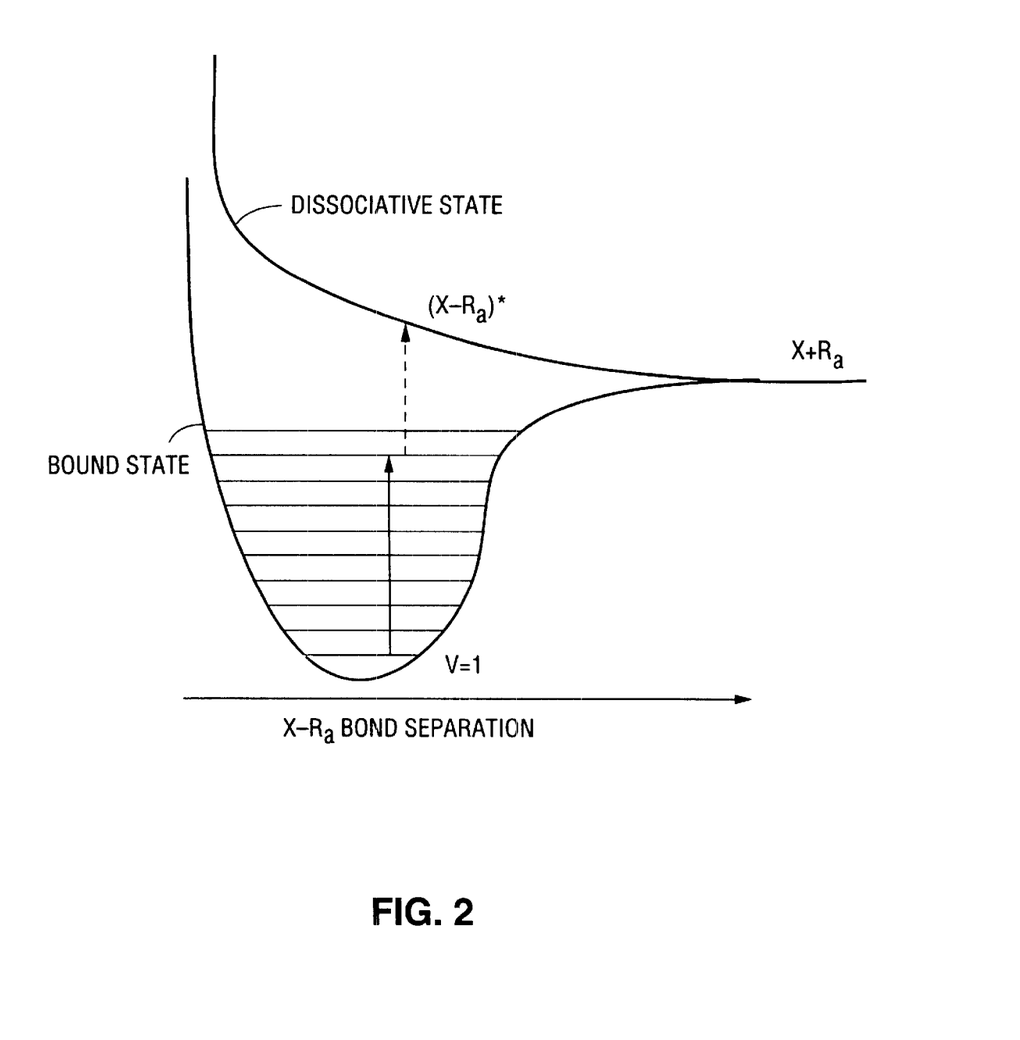
FIG. 2 show a ground state potential energy diagram for the X—R bond in hypothetical molecule XR.

FIG. 2 is a potential energy diagram for a single vibrational/rotational state in a bond on hypothetical molecule, X—R.

In FIG. 2, X represents an atom or molecule in the substrate or the near-surface (top ~5 nanometers) bonding of the adsorbate to the substrate while R represents the sought after species within the adsorbate. The ordinate in this plot is the potential energy of the bound molecule while the abscissa is the internuclear separation of X and R. Excitation of vibrational/rotational transitions can drive the potential energy of the ground state into a dissociative state in which the molecule fragments into two components, X+R.

The incidence angle of the laser irradiation to the surface for this multiphoton absorption process can be varied to achieve different extents of cleavage of adsorbate/substrate bonds. For example, normal incidence irradiation in which the laser beam is normal (at 90°) to the sample surface may enhance breaking of adsorbate/substrate bonds only with the area of the surface subtended by the laser beam. Incidence at or near the critical angle (41.8° for glass/air interfaces) could promote multiple internal reflections of the laser irradiation within a glass substrate and lead to multiple points of cleavage of adsorbate/substrate bonds. In another embodiment, absorption of one or more photons of electromagnetic radiation promoting electronic excitation of adsorbate/substrate bond(s) followed by absorption of one or more infrared photons of electromagnetic radiation to selectively dissociate this electronically excited species can be utilized.

Figure 3:
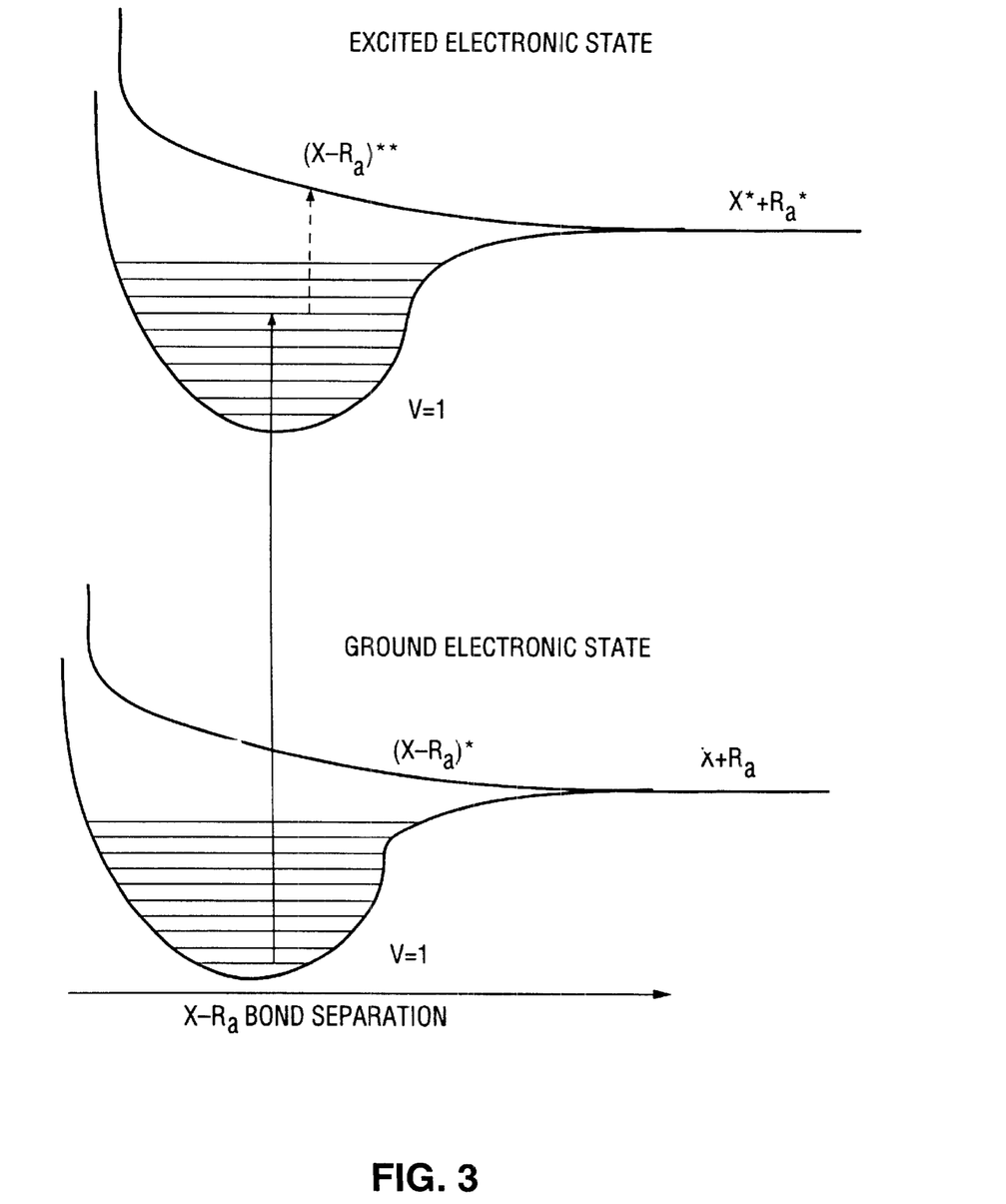
FIG. 3 shows ground and excited potential energy surfaces for the X—R bond in hypothetical molecule XR.

Electronic excitation of adsorbate/substrate bond(s) is typically achieved using electromagnetic radiation at infrared, visible, ultraviolet or X-ray wavelengths (~10,000 nanometers (nm) to <10 nm). FIG. 3 is a potential energy diagram of two electronics states of the hypothetical molecule X—R.

In FIG. 3, each electronic state is characterized by one or more vibrational/rotational states. Electronic excitation drives the X—R molecule into an electronic excited state, (X—R)*, which can either dissociate into fragments or remain intact. Subsequent absorption of infrared radiation by the (X—R)* state could lead to fragmentation of the stable, electronically excited molecule.

In yet another embodiment, absorption of one or more photons of electromagnetic radiation promoting vibrational and rotational excitation of adsorbate/substrate bond(s) followed by absorption of electromagnetic radiation promoting electronic excitation of these bonds into dissociative bond states can be utilized. This cleavage mechanism is the inverse of the one described above, i.e., the molecule is first put into an excited vibrational/rotational level and then electronically excited into a dissociative state.

Selection of Electromagnetic Radiation Wavelength

A wavelength (or frequency) must be selected for the desorbing laser. There are several ways to select the proper wavelength or frequency for the desorbing laser.

Initially, one of the known vibrational frequencies of the selected compound in its "pure" (unbound) gas/liquid or solid state can be utilized. These frequencies are available from a number of compilations including the electronic states of atoms from the National Institutes of Science and Technology (NIST, Gaithersburg, Md.), UV/visible spectroscopy and infrared absorption compilations produced by a number of companies including Aldrich Chemical Corporation(Milwaukee, Wis.) and Perkin-Elmer Corporation (Norwalk, Conn.) which are hereby incorporated by reference. The physical state of the standard will be its state at standard temperature and pressure conditions (room temperature, 1 atmosphere pressure.)

Next, measured vibrational/rotational or electronic transitions from a film of the sample chemically bound to a surface can be utilized. The former is measured with a Fourier Transform Infrared (FT-IR) spectrometer or a Raman spectrometer while the latter can be measured on a UV/Visible spectrophotomer. These instruments are commercially available. For samples where it is impossible to measure vibrational frequencies of the molecule bound to a surface, or get its standard state rotational/vibrational spectroscopy, theoretical data or chemical intuition can be utilized.

Application of the Methods of the Invention

There are many possible combinations of electromagnetic radiation which can achieve the desired adsorbate/substrate bond(s) cleavage. These combinations depend on the adsorbate/substrate bond strength, the nature of the bonds within the adsorbate and the manifold of vibrational/rotational and electronic transitions for the particular bond.

An example of one possible system is the bonding of organic silicon compounds (—Si—R)$_a$ to silicon oxide (—Si—O—)$_s$ moieties characteristic of inorganic silicon or glass surfaces. "R" refers to the organic moiety bound to a silicon atom on the adsorbate which is designated as "a" while (—Si—O—)$_s$ refers to the Si and oxygen bond of the substrate. The targeted bonds to cleave in this system could include the bond between the substrate oxygen and the adsorbate silicon species, (—Si—O)$_s$⇆(Si—R)$_a$; the bond between the substrate oxygen and the silicon substrate, (—Si⇆O)$_s$—(Si—R)$_a$; the bond between the adsorbate silicon and the R moiety, (—Si—O)$_s$—(Si⇆R)$_a$ or a selected bond within R. For example, vibrational/rotational excitation of the Si$_s$—O$_s$—Si$_a$— bond can use the strong asymmetric stretch transition in the infrared region of electromagnetic spectrum in the 8.8496 to 10.000 micrometer ($\mu$m) range. Absorption of n photons (n>20) in this region of the spectrum could excite bond vibrations into one or more dissociative states. Molecules dissociated from the substrate via this vibrational/rotational excitation include —Si$_s$—O$_s$—Si—R, —O$_s$—Si—R, —Si—R and —R. Multiphoton absorption can be achieved using an infrared laser tuned to the correct wavelength to excite the desired vibrational/rotational levels. These wavelengths can be determined as discussed above.

Selective Bond Cleavage Using Multiple Wavelengths

Bond cleavage by electronic excitation alone or in combination with vibrational/rotational excitation can be achieved using visible or ultraviolet laser radiation to pump the ground state molecule into an electronic excited state. Bond cleavage via intra-molecule energy transfer following electronic excitation may occur for certain bonds. More controllable bond cleavage can be achieved using a second infrared laser to promote multiphoton absorption by vibrational/rotational transitions of this excited molecule. Electronic excitation can be achieved using pulsed laser systems operating in the wavelength region from 150 nm to –400 nm. Such lasers include gas lasers (excimer and rare gas such as Ar ion lasers) and solid state lasers such as Nd:YAG, titanium sapphire (Ti:sapphire) and Erbium (Er) lasers as well as more sophisticated lasers such as free electron lasers.

Selective Bond Cleavage Using Particles

Particle bombardment can also be used for selective bond cleavage. In this embodiment the adsorbate/substrate system is bombarded with a particle beams to promote excitation of chemical bonds in the adsorbate/substrate system similar to those described above for excitation by electromagnetic radiation. In this embodiment, all or part of the initial impact energy or internal excitation energy of the particle beam is converted into vibrational/rotational bond excitation, electronic excitation or some combination of these two modes of excitation leading to selective cleavage of adsorbate/substrate bond(s).

Energetic particle bombardment of an adsorbate bound to a substrate can also lead to selective cleavage of adsorbate/substrate bond(s). Examples of energetic particles used for this type of selective bond cleavage include bombardment by energetic electrons, positrons, positive or negative elemental ions or neutral atoms as well as positive or negative molecular or cluster ions as well as energetic neutral molecules. Important requirements for selective bond cleavage induced by particle bombardment are selecting optimal particle beam bombardment energy(ies), particle type and intensity(ies) to match a resonant cleavage channel for the X—R bond such that efficient energy transfer occurs between the particle beam and the adsorbate/substrate bond(s).

Particle beam desorption may be used in conjunction with selective bond cleavage by absorption of electromagnetic radiation in the system as described above which may lead to an increase in the desorption yield. This combination may result in a method of micrometer or nanometer scale analysis in which the probed area can be determined by the size of the probe particle beam. This type of analysis can also apply to laser beam excitation of the vibrational modes of the bound molecule.

Mass Analysis Processes

Once the desired molecular species are desorbed from the substrate in the form of neutral molecules or fragments as well as possible positively or negatively charged ions, the neutral components will be selectively ionized into either positive or negative ions and the mass and intensity of intact molecular ions and or their representative fragment ions will be determined using various mass spectrometric techniques. Representative ionization methods for producing molecular or characteristic fragment ions from desorbed neutrals include:

1. electron impact ionization
2. resonance or non-resonant multiphoton ionization
3. chemical ionization methods and
4. charge transfer ionization All of these ionization techniques are well known and can provide the necessary efficiency required to produce detectable ion signals from the cleaved neutral species.

Representative mass spectrometry techniques for this invention include quadruple, ion trap, and Fourier transform mass spectrometry; single and double focusing mass spectrometric techniques, ion mobility spectrometry and time-of-flight mass spectrometry.

In another embodiment of the invention a complete system for selective bond cleavage and mass spectrometric analysis of cleaved neutrals can couple resonant multiphoton bond cleavage with electron impact ionization of the neutrals and time-of-flight mass spectrometric analysis of the positive ions formed.

Areas of Application

Selective bond cleavage processes followed by mass spectrometric analysis of cleaved neutral species has its most general applications in areas in which the chemical composition of thin layers bound to solid surfaces is of primary importance. Specific applications of this technique include combinatorial chemistry, self-assembled monolayers, semiconductor processing and membrane analysis.

Combinatorial Chemistry

This invention provides a selective method of chemical analysis of organic and inorganic products formed in solid phase syntheses using various methods including combinatorial synthesis of a large range of organic and inorganic compounds. Included in this list are peptides, proteins, oligonucleotides, genomic materials and inorganic complexes. Combinatorial syntheses employ solid supports (substrates) to which is bound specific linker molecules providing the bond or link between the the substrate and the incipient compound synthesized by a variety of combinatorial methods. Chemical synthesis is subsequently performed on this linker. Selective cleavage of the linker/substrate bond or bonds near the point of attachment of the linker to the substrate followed by mass spectrometric analysis of these cleaved molecules can provide sensitive, localized and selective chemical analysis of the synthesis products.

A specific example of the potential utility of this type of selective bond cleavage is exemplified by the system for combinatorial synthesis of oligonucleotides developed by Pease et al (*Proc. Natl. Acad. Sci*, 91, pp.5022–5026, 1994). This system employs a glass substrate which is derivatized using bis(2 hydroxyethyl)aminopropyltriethoxysilane which binds to the glass surface through—$(Si-O)_s-Si_a$—bonds where—$(Si-O)_s$ refers to the glass substrate and —$Si_a$— refers to the silicon on the bis(2-hydroxyethyl) aminopropyltriethoxysilane. A linker molecule, typically 4,4'-dimethoxyhexaethyleneglycol-(2-cyano-N,N'-diisopropyl)phosphoramidite, is bound to the aminopropyl end of the silane. The linker molecules links or binds the first oligonucleotide of a sequence and a patterned array of oligonucleotides are synthesized over the area of the surface bound to the linker using light-directed synthesis with or without a photoresist layer. Thus, a two-dimensional pattern or array of oligonucleotides in which each feature or cell contains a unique oligonucleotide sequence can be synthesized using this multiple step or combinatorial synthesis. Feature sizes for these systems currently are in the 5–10 micrometer range; however, photolithographic processes could reduce this feature size to ~1 micrometer. Selective bond cleavage followed by mass spectrometric analysis of the cleaved neutral molecules could provide a unique method of determining the mass of the sequenced oligonucleotides at each feature and thus would provide a method of site-specific chemical analysis.

One method of achieving selective, site-specific bond cleavage of the oligonucleotides is to selectively break the —(Si—O)$_s$—Si$_a$— bonds between the glass substrate and the derivatizing reagent.

Selective bond cleavage can be achieved using a focused, infrared laser operating at wavelengths in the 8.8496 to 10.0000 micrometer range which is unique for asymmetric stretch vibrations of the —Si—O—Si— bond (R. M. Silverstein, G. C. Bassler and T. C. Morrill, *Spectrometric Identification of Organic Compounds*, 3rd Edition, Wiley & Sons, New York, 1974). This wavelength region will excite asymmetric stretch vibrations of the —Si—O—Si— bond and the absorption of multiple photons of the exciting laser light could lead to selective cleavage of this bond. The exact value of the optimum wavelength for this resonant infrared photocleavage will depend on the details of the glass-adsorbate bond and can be determined by scanning the wavelength of the infrared laser over this wavelength region. The optimum laser system for this measurement is a Pb-salt semiconductor laser which has a tuning range from 3.6 to 13 micrometer and is manufactured b Laser Photonics Inc. (Wilmington, Ma.). Sufficient power densities to dissociate —(Si—O)$_s$—Si$_a$— bonds will be achieved by pulsing the laser at short pulse widths (~1 microseconds). Site specific bond cleavage will be achieved by focusing the laser output to its diffraction limit at the glass surface(~13 micrometer diameter at 10 micrometer wavelength) and rastering or scanning this focused laser beam over the active area of the glass.

Analysis of Self Assembled Monolayers

The methods of this invention can be utilized for analysis of self-assembled monolayers (SAMs) and other single or multiple monolayer films which are chemically bound to a substrate. These applications include characterization of the composition and distribution of lubricant molecules on surfaces for tribological (wear and friction) applications, especially with regard to determining the change in composition of these lubricants as a function of wear (heat, friction, loads). SAMs are also employed extensively in various biomaterials to provide an intermediate or buffer layer at the interface between the cells, tissues or organs characteristic of the host organism and the biomaterial. The proposed invention could provide a rapid, reproducible method for determining the chemical composition and uniformity of the SAM layer as well as provide a means for detecting reaction products produced in interactions of the host molecules with the molecules in the self assembled monolayer or the biomaterial substrate.

Surface Analysis in Semiconductor Electronics and Optical coatings Industries

The methods of this invention can be utilized for analysis of specific chemicals bound to inorganic substrates such as silicon or silicon oxide in applications in semiconductor electronics and optical coatings industries both in manufacturing and research and development activities. Selective bond cleavage can provide a unique method of identifying organic or inorganic contaminants on semiconductor silicon, III–V or II–VI substrates. This mode of characterization can also provide information on the extent of binding of specific organic or inorganic species to the substrate. For example, detection of selective molecules of photoresist at specific locations on a semiconductor silicon surface could provide a method of ascertaining the degree of photoresist removal in a variety of etching processes.

Chemical Characterization of Membrane Surfaces

The methods of this invention can be utilized for chemical characterization of membrane surfaces in which specific molecules preferentially bond to the surface. Membrane surfaces can be organic or inorganic and include such materials as filters used to purify liquids and gases, medical implants on which specific molecules preferentially bond, as well as plastic and glass contact lens which preferentially attract specific peptides and proteins.

This invention will be better understood by reference to the following non-linking Examples:

EXAMPLES

Example 1

An absorbate/substrate bond is selected from glass substrate/absorbate, metal substrates/adsorbates, carbonaceous substrate/absorbate and the like as described above. Transitions for resonant bond breaking are determined by identifying vibrational/rotational transitions or electronic transitions. Vibrational/rotational transitions are identified from FT-IR or Raman libraries, measured transitions from thick film standards of analyte specimens or from reasonable estimates for comparable bonds. Electronic transitions are identified from UV-Visible Spectroscopy libraries, measured experimental data or reasonable estimates.

Once the transition for resonant bond breaking has been determined, a specimen is inserted into the ion source of a mass spectrometer equipped with necessary IR, visible or UV pulsed lasers focused through the vacuum wall onto the sample surface area. The instrument is also equipped with ion, electron, and/or laser sources for ionizing cleaved, neutral molecules.

Once the specimen has been positioned, the specimen is irradiated at a glazing angle with the pulsed output of the bond cleavage laser followed by accurately timed pulses of the ionizing beam (laser, ion or electron) of controlled duration.

Ion intensity as function of ion mass data (mass spectra) for the irradiated surface is accumulated using one or more of mass spectrometry techniques listed above in order to identify chemical species cleaved from the surface.

Example 2

The method of Example 1 is followed except that energetic charge particle or neutral beams is utilized to cleave the substrate/absorbate bonds.

What is claimed is:

1. A method for desorbing an adsorbate bound or bonded to a substrate wherein the adsorbate/substrate system includes at least two energy levels, the method comprising the steps of
   (a) selecting an electromagnetic wavelength that is approximately resonant with a transition between a first energy level and a second energy level; and
   (b) irradiating the adsorbate/substrate system with electromagnetic radiation at the selected wavelength thereby cleaving a bond in the adsorbate/substrate system,
      wherein the substrate is glass, and
      wherein the cleaved bond is selected from the group consisting of a silicon-oxygen substrate bond, a silicon-carbon adsorbate bond, a silicon-heteroatom adsorbate bond and a silicon-oxygen adsorbate/substrate bond.

2. A method for desorbing an adsorbate molecule bonded to a substrate via a -silicon-oxygen-silicon- moiety, the method comprising selectively exciting the asymmetric stretch of the -silicon-oxygen-silicon- moiety to cleave a silicon-oxygen bond within the -silicon-oxygen-silicon- moiety.

3. The method according to claim 2 wherein the asymmetric stretch of the -silicon-oxygen-silicon- moiety is excited using a laser.

4. The method according to claim 3 wherein the laser operates at wavelengths between about 8.85 and about 10.00 micrometers.

5. The method according to claim 4 wherein the laser is a pulsed laser with a pulse width of less than about one microsecond.

* * * * *